United States Patent [19]

King

[11] Patent Number: 4,882,327
[45] Date of Patent: Nov. 21, 1989

[54] CERTAIN HETEROCYCLIC N-SUBSTITUTED CARBOXAMIDES

[75] Inventor: Francis D. King, Essex, England

[73] Assignee: Beecham Group p.l.c., Middlesex, England

[21] Appl. No.: 185,111

[22] Filed: Apr. 22, 1988

[30] Foreign Application Priority Data

Apr. 25, 1987 [GB] United Kingdom ............. 8709857
May 5, 1987 [GB] United Kingdom ............. 8710570
Jul. 14, 1987 [GB] United Kingdom ............. 8716530
Jan. 16, 1988 [GB] United Kingdom ............. 8800982

[51] Int. Cl.$^4$ ............. A61K 31/44; C07D 471/04
[52] U.S. Cl. ............. 514/214; 514/299; 514/300; 514/304; 514/305; 546/112; 546/121; 546/126; 546/133.3; 546/137; 546/183
[58] Field of Search ............. 546/112, 121, 126, 133, 546/137, 183; 540/582; 514/214, 299, 300, 304, 305

[56] References Cited

U.S. PATENT DOCUMENTS 4,789,673 12/1988 Donatsch et al. ............. 546/126

FOREIGN PATENT DOCUMENTS 0158265 10/1985 European Pat. Off.
0200444 11/1986 European Pat. Off.
2100259 12/1982 United Kingdom.
2125398 3/1984 United Kingdom.

Primary Examiner—Mary C. Lee
Assistant Examiner—Bernard I. Dentz
Attorney, Agent, or Firm—Hopgood, Calimafde, Kalil, Blaustein & Judlowe

[57] ABSTRACT

Compounds of formula (I), or a pharmaceutically acceptable salt thereof:

Y-CO-L-Z  (I)

wherein
L is NH or O; Y is a group of formula (a), (b) or (c):

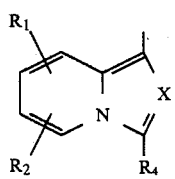

(a)

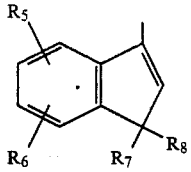

(b)

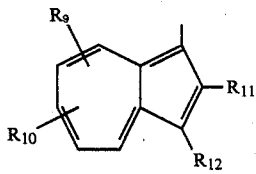

(c)

wherein
$R_1$ and $R_2$, $R_5$ and $R_6$, $R_9$ and $R_{10}$, are independently selected from hydrogen or halogen;
X is N or $CR_3$ wherein
$R_3$ is hydrogen or $C_{1-6}$ alkoxy;
$R_4$ is hydrogen, halogen, $CF_3$, $C_{1-6}$ alkyl, $C_{1-6}$ alkoxy, $C_{1-6}$ alkylthio, $C_{1-6}$ alkylsulphonyl, $C_{1-6}$ alkylsulphinyl, $C_{1-7}$ acyl, cyano, $C_{1-6}$ alkoxycarbonyl, $C_{1-7}$ acylamino, hydroxy, nitro or amino, aminocarbonyl, or aminosulphonyl, optionally N-substituted by one or two groups selected from $C_{1-6}$ alkyl, $C_{3-8}$ cycloalkyl, and $C_{3-8}$ cycloalkyl $C_{1-4}$ alkyl or disubstituted by $C_4$ or $C_5$ polymethylene; phenyl or phenyl $C_{1-4}$ alkyl group optionally substituted in the phenyl ring by one or two of halogen, $C_{1-6}$ alkoxy or $C_{1-6}$ alkyl groups;
one of $R_7$ and $R_8$ is $C_{1-6}$ alkyl and the other is $C_{1-6}$ alkyl, phenyl or phenyl $C_{1-4}$ alkyl optionally substituted in either phenyl ring by one or two of $C_{1-6}$ alkoxy or halogen; or
$R_7$ and $R_8$ together are $C_{2-6}$ polymethylene or $C_{2-5}$ polymethylene interrupted by an -O- linkage;
$R_{11}$ is hydrogen or $C_{1-6}$ alkoxy;
$R_{12}$ is hydrogen, halogen, $CF_3$, $C_{1-6}$ alkyl, $C_{1-6}$ alkoxy, $C_{1-6}$ alkylthio, $C_{1-6}$ alkylsulphonyl, $C_{1-6}$ alkylsulphinyl, $C_{1-7}$ acyl, cyano, $C_{1-6}$ alkoxycarbonyl, $C_{1-7}$ acylamino, hydroxy, nitro or amino, aminocarbonyl, or aminosulphonyl, optionally N-substituted by one or two groups selected from $C_{1-6}$ alkyl, $C_{3-8}$ cycloalkyl, and $C_{3-8}$ cycloalkyl $C_{1-4}$ alkyl or disubstituted by $C_4$ or $C_5$ polymethylene; phenyl or phenyl $C_{1-4}$ alkyl optionally substituted in either phenyl ring by one or two of halogen, $C_{1-6}$ alkoxy or $C_{1-6}$ alkyl groups; Z is a group of formula (d), (e) or (f):

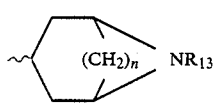

(d)

(Abstract continued on next page.)

-continued
(e) 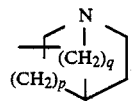
(f) 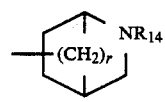
wherein
n is 2 or 3;
p is 1 or 2;
q is 1 to 3;
r is 1 to 3; and
$R_{13}$ and $R_{14}$ is $C_{1-4}$ alkyl; having 5-$HT_3$ receptor antagonist activity, a process for their preparation and their use as pharmaceuticals.
9 Claims, No Drawings

CERTAIN HETEROCYCLIC N-SUBSTITUTED CARBOXAMIDES

This invention relates to novel compounds having useful pharmacological properties, to pharmaceutical compositions containing them, to a process and intermediates for their preparation, and to their use as pharmaceuticals.

GB No. 2100259A and 2125398A, EP-A-Nos. 158265 and 200444 describe compounds having 5-HT$_3$ receptor antagonist activity.

A class of novel, structurally distinct compounds has now been discovered. These compounds have 5-HT$_3$ receptor antagonist activity.

Accordingly, the present invention provides a compound of formula (I), or a pharmaceutically acceptable salt thereof:

Y-CO-L-Z     (I)

wherein
L is NH or O;
Y is a group of formula (a), (b) or (c):

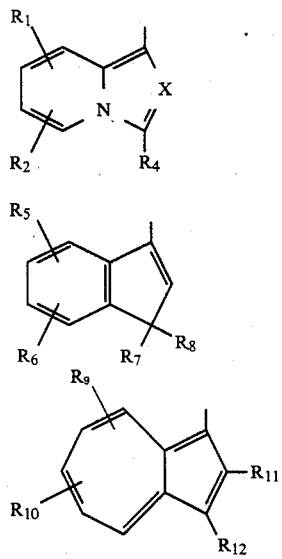

wherein
R$_1$ and R$_2$, R$_5$ and R$_6$, R$_9$ and R$_{10}$, are independently selected from hydrogen or halogen;
X is N or CR$_3$
wherein
R$_3$ is hydrogen or C$_{1-6}$ alkoxy;
R$_4$ is hydrogen, halogen, CF$_3$, C$_{1-6}$ alkyl, C$_{1-6}$ alkoxy, C$_{1-6}$ alkylthio, C$_{1-6}$ alkylsulphonyl, C$_{1-6}$ alkylsulphinyl, C$_{1-7}$ acyl, cyano, C$_{1-6}$ alkoxycarbonyl, C$_{1-7}$ acylamino, hydroxy, nitro or amino, aminocarbonyl, or aminosulphonyl, optionally N-substituted by one or two groups selected from C$_{1-6}$ alkyl, C$_{3-8}$ cycloalkyl, and C$_{3-8}$ cycloalkyl C$_{1-4}$ alkyl or disubstituted by C$_4$ or C$_5$ polymethylene; phenyl or phenyl C$_{1-4}$ alkyl group optionally substituted in the phenyl ring by one or two of halogen, C$_{1-6}$ alkoxy or C$_{1-6}$ alkyl groups;
one of R$_7$ and R$_8$ is C$_{1-6}$ alkyl and the other is C$_{1-6}$ alkyl, phenyl or phenyl C$_{1-4}$ alkyl optionally substituted in either phenyl ring by one or two of C$_{1-6}$ alkyl, C$_{1-6}$ alkoxy or halogen; or
R$_7$ and R$_8$ together are C$_{2-6}$ polymethylene or C$_{2-5}$ polymethylene interrupted by an —O— linkage;
R$_{11}$ is hydrogen or C$_{1-6}$ alkoxy;
R$_{12}$ is hydrogen, halogen, CF$_3$, C$_{1-6}$ alkyl, C$_{1-6}$ alkoxy, C$_{1-6}$ alkylthio, C$_{1-6}$ alkylsulphonyl, C$_{1-6}$ alkylsulphinyl, C$_{1-7}$ acyl, cyano, C$_{1-6}$ alkoxycarbonyl, C$_{1-7}$ acylamino, hydroxy, nitro or amino, aminocarbonyl, or aminosulphonyl, optionally N-substituted by one or two groups selected from C$_{1-6}$ alkyl, C$_{3-8}$ cycloalkyl, and C$_{3-8}$ cycloalkyl C$_{1-4}$ alkyl or disubstituted by C$_4$ or C$_5$ polymethylene; phenyl or phenyl C$_{1-4}$ alkyl optionally substituted in either phenyl ring by one or two of halogen, C$_{1-6}$ alkoxy or C$_{1-6}$ alkyl groups;
Z is a group of formula (d), (e) or (f):

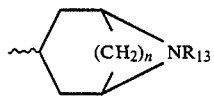   (d)

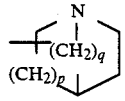   (e)

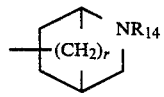   (f)

wherein
n is 2 or 3;
p is 1 or 2;
q is 1 to 3;
r is 1 to 3; and
R$_{13}$ or R$_{14}$ is C$_{1-4}$ alkyl.

Often L is NH.

Values for R$_1$ and/or R$_2$, R$_5$ and R$_6$, R$_9$ and R$_{10}$, include hydrogen, fluoro, chloro or bromo. Preferably R$_1$ and R$_2$, R$_5$ and R$_6$, R$_9$ and R$_{10}$, are both hydrogen.

Suitable values for X include N, or CR$_3^1$ wherein R$_3^1$ is hydrogen, methoxy, ethoxy, n- or iso-propoxy. Often X is N, CH or COMe.

Suitable values for R$_4$ include hydrogen, fluoro, chloro, bromo, CF$_3$, methyl, ethyl, methoxy, ethoxy, methylthio, ethylthio, methylsulphonyl, ethylsulphonyl, methylsulphinyl, ethylsulphinyl, acetyl, propionyl, cyano, methoxycarbonyl, ethoxycarbonyl, acetylamino, hydroxy, nitro; and amino, aminocarbonyl, or aminosulphonyl, any of which may be optionally substituted by one or two methyl groups or by a cyclopentyl or cyclohexyl group or R$_4$ is phenyl or benzyl optionally substituted in the phenyl ring, by one or two methyl, methoxy, bromo, chloro or fluoro groups.

Suitable values for alkyl groups in R$_7$ and R$_8$ include methyl, ethyl, n- and iso-propyl, n-, iso-, sec- and tert-butyl. Values for R$_7$/R$_8$ also include phenyl, or benzyl optionally substituted by one or two groups selected from methyl, methoxy, chloro, fluoro or bromo. Preferably R$_7$ and R$_8$ are both methyl groups.

When R$_7$ and R$_8$ are joined, suitable values for R$_7$/R$_8$ include C$_3$, C$_4$, C$_5$, C$_6$ and C$_7$ polymethylene; often C$_4$ or C$_5$ polymethylene.

Suitable values for R$_{11}$ include hydrogen, methoxy, ethoxy, n- or iso-propoxy.

Suitable values for $R_{12}$ include hydrogen, fluoro, chloro, bromo, $CF_3$, methyl, ethyl, methoxy, ethoxy, methylthio, ethylthio, methylsulphonyl, ethylsulphonyl, methylsulphinyl, ethylsulphinyl, acetyl, propionyl, cyano, methoxycarbonyl, ethoxycarbonyl, acetylamino, hydroxy, nitro; and amino, aminocarbonyl, or aminosulphonyl, any of which may be optionally substituted by one or two methyl groups or by a cyclopentyl or cyclohexyl group or $R_{12}$ is phenyl or benzyl optionally substituted by one or two methyl, methoxy, bromo, chloro or fluoro groups.

Preferably n is 2 or 3 and p, q and r are 1 or 2.

Examples of $R_{13}/R_{14}$ include as groups of interest $C_{1-3}$ alkyl such as methyl, ethyl and N- and iso-propyl. $R_{13}/R_{14}$ is preferably methyl or ethyl, most preferably methyl.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric. α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid.

Preferably the acid addition salt is the hydrochloride salt.

Examples of pharmaceutically acceptable salts include quaternary derivatives of the compounds of formula (I) such as the compounds quaternised by compounds $R_a$-T wherein $R_a$ is $C_{1-6}$ alkyl, phenyl-$C_{1-6}$ alkyl or $C_{5-7}$ cycloalkyl, and T is a radical corresponding to an anion of an acid. Suitable examples of $R_a$ include methyl, ethyl and n- and iso-propyl; and benzyl and phenethyl. Suitable examples of T include halide such as chloride, bromide and iodide.

Examples of pharmaceutically acceptable salts also include internal salts such as N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

It will of course be realized that some of the compounds of the formula (I) have chiral or prochiral centres and thus are capable of existing in a number of stereoisomeric forms including enantiomers. The invention extends to each of these stereoisomeric forms (including enantiomers), and to mixtures thereof (including racemates). The different stereoisomeric forms may be separated one from the other by the usual methods.

It will also be realized that compounds of formula (I) may adopt an endo or exo configuration with respect to L. The endo configuration is preferred.

A group of compounds within formula (I) is of formula (II):

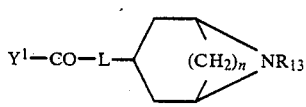

(II)

wherein $Y^1$ is a group of formula (a) wherein X is N, CH or C—$COCH_3$, or a group of formula (b) or (c), as defined in formula (I).

Examples of the variables and preferred variables are as so described for corresponding variables in relation to formula (I).

A further group of compounds within formula (I) is of formula (III):

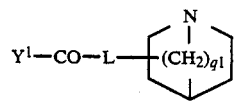

(III)

wherein $q^1$ is 1 or 2 and the remaining variables are as defined in formulae (I) and (II).

Examples of the variables and preferred variables are as so described for the corresponding variables in formula (I).

There is a further group of compounds within formula (I) of formula (IV):

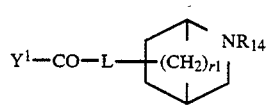

(IV)

wherein $r^1$ is 1 or 2 and the remaining variables are as defined in formulae (I) and (II).

Examples of the variables and preferred variables are so described as the corresponding variables in formula (I).

The invention also provides a process for the preparation of a compound of formula (I), or a pharmaceutically acceptable salt thereof, which process comprises reacting a compound of formula (V):

Y—$COQ_1$  (V)

with a compound of formula (VI):

H-L-$Z^1$  (VI)

or a reactive derivative thereof, when L is O; wherein $Q_1$ is a leaving group; $Z^1$ is Z as defined or Z wherein $R_{13}/R_{14}$ is replaced by a hydrogenolysable protecting group; and the remaining variables are as hereinbefore defined; and thereafter optionally converting any $R_1$ and/or $R_2$, $R_5$ and/or $R_6$, $R_9$ and/or $R_{10}$ group to another $R_1/R_2$, $R_5/R_6$, $R_9/R_{10}$ group respectively, converting $Z^1$, when other than Z, to Z; and optionally forming a pharmaceutically acceptable salt of the resultant compound of formula (I).

Examples of leaving groups $Q_1$, displaceable by a nucleophile, include halogen such as chloro and bromo, $C_{1-4}$ alkoxy, such as $CH_3O$ and $C_2H_5O$—, PhO—, or activated hydrocarbyloxy, such as $Cl_5C_6O$— or $Cl_3CO$—

If a group $Q_1$ is a halide, then the reaction is preferably carried out at non-extreme temperatures in an inert non-hydroxylic solvent, such as benzene, dichloromethane, toluene, diethyl ether, tetrahydrofuran (THF) or dimethylformamide (DMF).

It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°–100° C., in particular 10°–80° C. are suitable.

If a group $Q_1$ is $C_{1-4}$ alkoxy, phenoxy or activated hydrocarbyloxy then the reaction is preferably carried out in an inert polar solvent, such as toluene or dimethylformamide. It is also preferred that the group $Q_1$ is $Cl_3CO—$ and that the reaction is carried out in toluene at reflux temperature.

When L is O the compound of formula (VI) may be in the form, of a reactive derivative thereof, which is often a salt, such as the lithium, sodium or potassium salt.

It will be apparent that compounds of the formula (I) containing an $R_1$ or $R_2$, $R_5$ or $R_6$, $R_9$ or $R_{10}$ group which is convertible to another $R_1$ or $R_2$, $R_5$ or $R_6$, $R_9$ or $R_{10}$ group are useful novel intermediates. i.e. a hydrogen substituent is convertible to a halogen substituent by halogenation using conventional halogenating agents.

$Z^1$ when other than Z may have a hydrogenolysable protecting group which is benzyl optionally substituted by one or two groups as defined for $R_7/R_8$ when phenyl. Such benzyl groups may, for example, be removed, when $R_1$ or $R_2$, $R_5$ or $R_6$, $R_9$ or $R_{10}$ is not halogen, by conventional transition metal catalyzed hydrogenolysis to give compounds of the formula (VII):

$$Y\text{-CO-L-}Z^2 \qquad (VII)$$

wherein $Z^2$ is of formula (g) or (h):

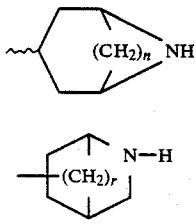

wherein the variables are as defined in formula (I).

This invention also provides a further process for the preparation of a compound of the formula (I) which comprises N-alkylating a compound of formula (VII), and optionally forming a pharmaceutically acceptable salt, of the resulting compound of the formula (I).

In this further process of the invention 'N-alkylation' comprises the substitution of the N-atom depicted in formula (VII) by any group $R_{13}/R_{14}$ as hereinbefore defined. This may be achieved by reaction of the compound of formula (VII) with a compound $R_{13}Q_3$ or $R_{14}Q_3$ wherein $R_{13}$ and $R_{14}$ are as hereinbefore defined and $Q_3$ is a leaving group.

Suitable values for $Q_3$ include groups displaced by nucleophiles such as Cl, Br, I, $OSO_2CH_3$ or $OSO_2C_6H_4pCH_3$.

Favored values for $Q_3$ include Cl, Br and I.

The reaction may be carried out under conventional alkylation conditions for example in an inert solvent such as dimethylformamide in the presence of an acid acceptor such as potassium carbonate. Generally the reaction is carried out at non-extreme temperature such as at ambient or slight above.

Alternatively, 'N-alkylation' may be effected under conventional reductive alkylation conditions when the group $R_{13}$ or $R_{14}$ in the compound of formula (I) contains a methylene group adjacent to the N-atom in the bicycle.

Interconverting $R_{13}$ or $R_{14}$ in the compound of the formula (VII) before coupling with the compound of the formula (V) is also possible. Such interconversions are effected conveniently under the above conditions. It is desirable to protect any amine function with a group readily removable by acidolysis such as a $C_{2-7}$ alkanoyl group, before $R_{13}/R_{14}$ interconversion.

When $R_{13}$ or $R_{14}$ in the compound of formula (VI) contains a methylene group adjacent to the N-atom in the bicycle it is often convenient in the preparation of such a compound of formula (VI) to prepare the corresponding compound wherein the methylene group is replaced by —CO—, or for $R_{13}$ or $R_{14}$ is methyl, where the methyl group is replaced by alkoxycarbonyl. Such compounds may then be reduced using a strong reductant such as lithium aluminium hydride to the corresponding compound of formula (V).

The compounds of formula (V) and (VI) are known or are preparable analogously to, or routinely from, known compounds.

Compounds of formula (VII) are novel and form an aspect of the invention.

It will be realized that in the compound of the formula (I) the—CO—L— linkage may have an endo or exo orientation with respect to the ring of the bicyclic moiety to which it is attached. A mixture of endo and exo isomers of the compound of the formula (I) may be synthesized non-stereo specifically and the desired isomer separated conventionally therefrom e.g. by chromatography; or alternatively the endo and exo isomer may if desired by synthesized from the corresponding endo or exo form of the compound of the formula (VI).

Pharmaceutically acceptable salts of the compounds of this invention may be formed conventionally.

The salts may be formed for example by reaction of the base compound of formula (I) with a pharmaceutically acceptable organic or inorganic acid.

The compounds of the present invention are 5-HT$_3$ receptor antagonists and it is thus believed may generally be used in the treatment or prophylaxis of migraine, cluster headaches and trigeminal neuralgia; visceral pain; and also as anti-emetics, in particular that of preventing vomiting and nausea associated with cancer therapy, and motion sickness. Examples of such cancer therapy include that using cytotoxic agents, such as cisplatin, doxorubicin and cyclophosphamide, particularly cisplatin; and also radiation treatment. Compounds which are 5-HT$_3$ receptor antagonists may also be of potential use in the treatment of CNS disorders such as anxiety and psychosis; arrhythmia, obesity and gastrointestinal disorders, such as irritable bowel syndrome.

The invention also provides a pharmaceutical composition comprising a compound of formula (I), or a pharmaceutically acceptable salt thereof, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavorings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavoring or coloring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavoring or coloring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilizing before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum Parenteral suspensions are prepared in substantially the same manner except that the compound is suspended in the vehicle instead of being dissolved and sterilized by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of migraine, cluster headache, trigeminal neuralgia and/or emesis in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.05 to 1000 mg for example 0.5 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated at any of the aforementioned dosage ranges.

The invention also provides a compound of formula (I) or a pharmaceutically acceptable salt thereof for use as an active therapeutic substance, in particular for use in the treatment of migraine, cluster headache, trigeminal neuralgia and/or emesis.

The following Examples illustrate the preparation of compounds of formula (I); the following descriptions illustrate the preparation of intermediates.

Description 1

3-Ethylindolizin-1-carboxylic acid (D1)

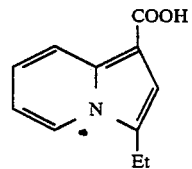

A solution of methyl 2-pyridylacetate (6 ml) 2,6-lutidine (6 ml) and 2-bromobutyraldehyde (5.5 g) (P. Duhamel, L. Duhamel, J-Y. Valnot, Bull. Soc. Chim. Fr. 1973(4) 1465) in xylene (200 ml) was heated under reflux overnight, removing water by means of a Dean and Stark apparatus. The reaction mixture was cooled, washed with dilute citric acid solution and the organic phase dried (Na$_2$SO$_4$) and concentrated. Column chromatography (SiO$_2$, CH$_2$Cl$_2$) of the residue afforded the methyl ester of the title compound (4.6 g). A solution of the ester (4.6 g) in EtOH (100 ml) and 1N NaOH (50 mL) was heated under reflux for 3h. The reaction mixture was cooled, the EtOH evaporated and the aqueous residue washed with Et$_2$O (50 mL). Acidification of the aqueous layer afforded the title compound (3.0 g).

Description 2

3-Methylindolizin-1-carboxylic acid (D2)

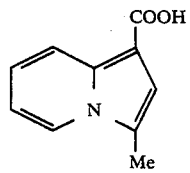

Following the procedures outlined in description 1,2-bromopropionaldehyde was converted to the title compound. m.p. 193°–5° C.

Description 3

3-Bromoindolizin-1-carboxylic acid (D3)

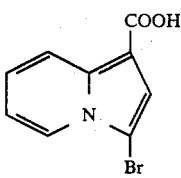

A solution of indolizin-1-carboxylic acid (prepared from the ethyl ester: D. R. Bragg, D. G. Wibberley, J. Chem. Soc., 1962, 2627) in glacial HOAc (50 mL) was treated with $Br_2$ (1.6 g) in HOAc (10 ml) at 10° C. After discharge of the $Br_2$ color, the solvent was removed and the residue partitioned between $Et_2O$ (20 mL) and 1N NaOH (50 mL). The aqueous layer was acidified to yield the title compound (D3), (0.8 g) m.p. >260° C.

$^1H$ Nmr (d6-DMSO) δ: 12.10 (brs, 1), 8.32 (d, 1), 8.11 (d, 1), 7.29 (s, 1), 7.25 (m, 1), 7.05 (t, 1).

Description 4

3-Ethylimidazo[1,5-a]pyridin-1-carboxylic acid (D4)

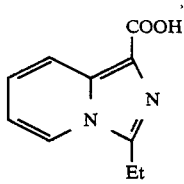

A solution of freshly prepared ethyl α-amino-α-(2-pyriyl)acetate (3.8 g) [G. van Zyl, D. L. Devries, R. H. Decker, E. T. Niles, J. Org. Chem., 26. 3373 (1961)] and propionic anhydride (4 ml) in $CH_2Cl_2$ (25 ml) was stirred at room temperature overnight. The solvent was removed and the residue partitioned between EtOAc (100 ml) and an excess of 10% $Na_2CO_3$ solution. The dried ($Na_2SO_4$) organic extract was concentrated and the residue heated under reflux for 18h with $POCl_3$ (1.2 ml) in $ClCH_2CH_2Cl$ (100 ml). The excess $POCl_3$ and solvent were removed by rotary evaporation and the residue partitioned between EtOAc (100 ml) and an excess of 10% $Na_2CO_3$ solution. Concentration of the dried organic extract afforded the ethyl ester of the title compound (4.0 g), purified by filtration through a TLC silica bed with $CH_2Cl_2$ as eluent. The ester was hydrolyzed with 1N NaOH (50 ml) in EtOH (50 ml) at reflux for 2h. The EtOH was removed by rotary evaporation and the pH of the aqueous residue adjusted to pH 4 with 5N HCl. The title compound was collected and dried (2.5 g).

Description 5

3-Trifluoromethylimidazo[1,5-a]pyridin-1-carboxylic acid (D5).

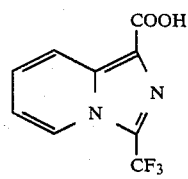

A mixture of freshly prepared ethyl α-amino-α-(2-pyridyl)acetate (0.8 g) was stirred with $(CF_3CO)_2O$ (5 ml) in $CH_2Cl_2$ (10 ml) for 3 days. The solvent and excess anhydride were removed by rotary evaporation and the residue hydrolyzed as described in Description 4 to give the title compound (0.6 g).

Description 6

3-Acetylindolizin-1-carboxylic acid (D6)

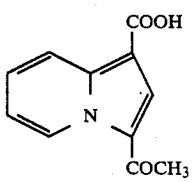

Base hydrolysis of ethyl 3-acetylindolizin-1-carboxylate (R. M. Acheson, M. G. Bite, M. W. Cooper, J. Chem. Soc. Perkin I, 1908 [1976]) as described for D1 gave the title compound D6.

EXAMPLE 1

(endo)-N-(8-Methyl-8-azabicyclo[3.2.1]oct-3-yl)indolizin-1-carboxamide (E1)

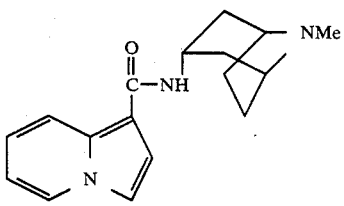

A solution of indolizin-1-carboxylic acid (0.32 g) in dry DMF (5 ml) at 0° C. was stirred with 1,1-carbonyldiimidazole (0.32 g) for 1h. A solution of (endo)-8-methyl-8-azabicyclo[3.2.1]octan-3-amine (0.32 g) in DMF (5 ml) was added and the reaction stirred to room temperature overnight. The solvent was removed by rotary evaporation and the residue partitioned between ethyl acetate (100ml) and 2.5N sodium hydroxide solution (50 ml). The organic layer was dried and concentrated and the residue purified by column chromatography ($Al_2O_3$; $CH_2Cl_2$–2% MeOH/$CHCl_3$) to give the title compound (0.24 g).

$^1H$-nmr ($CDCl^3$) 6 δ: 8.31 (d, 1H), 7.96 (d, 1H), 7.22 (d, 1H), 6.96 (t, 1H), 6.84 (d, 1H), 6.66 (t, 1H). 6.20 (brd, 1H), 3.27 (brs, 2H), 2.40–2.20 (m, 7H including 2.36, s, 3H), 2.00–1.80 (m, 4H), m.s. $M^+$ 283.1694; $C_{17}H_{21}N_3O$ requires 283.1661.

EXAMPLE 2

(endo)-N-(8-Methyl-8-azabicyclo[3.2.1]oct-3-yl)-3-ethylindolizin-1-carboxamide (E2)

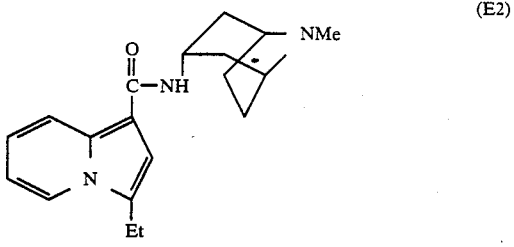

A solution of 3-ethylindolizin-1-carboxylic acid (1.0 g) in CH$_2$Cl$_2$ (100 ml) at 0° C. was treated with oxalyl chloride (0.46 ml). After stirring for 1h, a solution of (endo)-8-methyl-8-azabicyclo[3.2.1]octan-3-amine (0.75 g) and triethylamine (1.0 g) in CH$_2$Cl$_2$ (20 ml) was added and the whole stirred at room temperature for 2h. The reaction mixture was washed with saturated NaHCO$_3$ solution (2×50 ml), dried (K$_2$CO$_3$) and concentrated. The residue was crystallised from ethyl acetate/petrol to give the title compound (1.0 g). m.p. 182°-3° C.

$^1$H-Nmr (CDCl$_3$) δ: 8.33 (d, 1H), 7.78 (d, 1H), 6.95 (d,d,d, 1H), 6.70 (t, 1H), 6.60 (s, 1H), 6.18 (brd, 1H), 4.32 (q, 1H) 3.20 (brs, 2H, 2.82 (q, 2H), 2.40–2.10 (m, 7H including 2.32, s, 3H), 1.95–1.75 (m, 4H), 1.40 (t, 3H).

EXAMPLE 3

N-(3-Ouinuclidinyl)-3-ethylindolizin-1-carboxamide (E3)

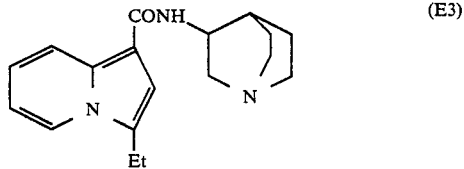

Following the procedure outlined in Example 2, 3-ethylindolizin-1-carboxylic acid (1.2 g) was converted to the title compound (0.9 g). m.p. 211°-2° C.

$^1$H Nmr (CDCl$_3$) δ: 8.33 (dm, 1), 7.78 (dm, 1), 6.96 (d,d,d, 1), 6.73 (s, 1), 6.70 (t d, 1), 5.98 (br d, 1), 4.27–4.15 (m, 1), 3.48 (d,dm 1), 3.05–2.76 (m, 6), 2.66 (dd, 1), 2.09 (m, 1), 90–1.40 (m, 4), 1.41 (t, 3).

EXAMPLES 4, 5

N-(2-Methyl-2-azabicyclo[2,2,2]oct-5-yl)-3-ethylindolizin-1-carboxamide: Isomer 1 (E4). Isomer 2 (E5)

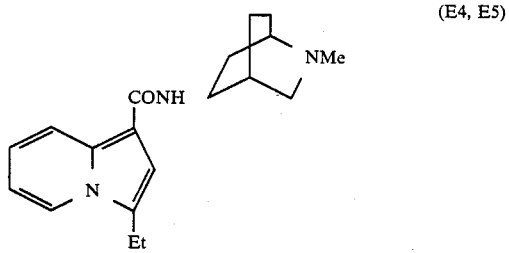

Following the procedure outlined in Example 2; 3-ethylindolizin-1-carboxylic acid (1.1 g) was reacted with a mixture of 5α,β-2-methyl-2-azabicyclo[2,2,2]octan-5-amine (0.9 g) (U.S. Pat. No. 4,533,498) to give a mixture of the title compounds E4 and E5 (1.7 g). Separation by column chromatography (SiO$_2$, 10MeOH/CHCl$_3$) afforded: (1) Isomer (1) E4 (0.07 g) m.p. 98°-103° C.

$^1$H-Nmr (CDCl$_3$) δ: 8.35 (dm, 1), 7.77 (d, 1), 7.20 (brs, 2), 6.93 (d,d,d, 1), 6.67 (t,d 1), 4.45–4.33 (m, 1), 3.56 (brd, 1), 2.92 (brs, 1), 2.81 (q, 2), 2.55 (s, 3), 2.43 (d, 1), 2.19 (dm, 3), 2.10–1.95 (m, 1), 1.80–1.70 (m, 2), 1.60–1.50 (m, 1), 1.41 (t, 3).

(2) Isomer (2) E5 (0.14 g)

$^1$H-Nmr (CDCl$_3$/d$^6$ DMSO) δ: 8.21 (dm, 1), 7.55 (brd, 1), 7.30 (s, 1), 6.96 (ddd, 1), 6.76 (t,d 1), 4.18–4.08 (m, 1), 2.86–2.76 (q+m, 3H), 2.29 (s, 3H), 1.35 (t, 3H).

EXAMPLE 6

(endo)-N-(8-Methyl-8-azabicyclo[3.2.1]oct-3-yl)-3-methylindolizin-1-carboxamide (E6)

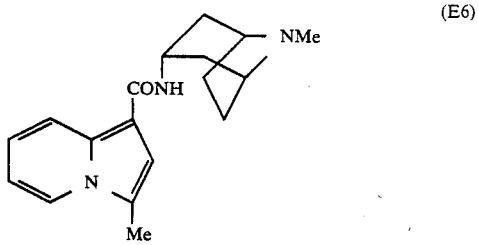

Following the procedures outlined in Example 2,3-methylindolizin-1-carboxylic acid (0.8 g) was converted to the title compound (E6) (0.83 g) m.p. 162°-5° C.

$^1$H-Nmr (CDCl$_3$) δ: 8.33 (dm, 1), 7.74 (d, 1), 6.96 (dt, 1), 6.71 (dt, 1), 6.61 (s, 1), 6.19 (brd, 1), 4.31 (q, 1), 3.20 (brs, 2), 2.57 (s, 3), 2.31 (s, 3), 2.38–2.15 (m, 4), 2.00–1.72 (m, 4).

EXAMPLE 7

(endo)-N-(8-Methyl-8-azabicyclo[3,2,1oct-3-yl-3-bromoindolizin-1-carboxamide (E7)

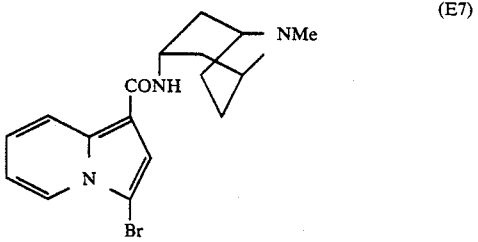

Following the procedures outlined in Example 2,3-bromoindolizin-1-carboxylic acid (0.4 g) was converted to the title compound (E7) (0.2 g) m.p. 186°-8° C.

$^1$H-Nmr (CDCl$_3$) δ: 8.33 (dm, 1), 8.04 (d, 1), 7.05 (d,d,m 1), 6.90 (s, 1), 6.82 (tm, 1), 6.20 (brd, 1), 4.30 (q, 1), 3.23 (brs, 2), 2.34 (s, 3), 2.38–2.10 (m, 4), 1.95–1.70 (m, 4).

EXAMPLE 8

(endo)-N-(9-Methyl-9-azabicyclo[3.3.1]non-3-yl)-3-ethylimidazo[1,5-a]pyridin-1-carboxamide (E8)

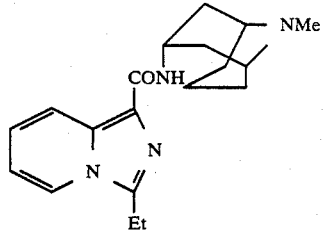

A suspension of 3-ethylimidazo[1,5-a]pyridin-1-carboxylic acid (D4) (0.22 g) in SOCl₂ (3 ml) was stirred at room temperature for 3h. The excess SOCl₂ was removed by rotary evaporation, the residue suspended in CH₂Cl₂ (10 ml) and treated with a solution of (endo)-9-methyl-9-azabicyclo[3,3,1]octan-3-amine (0.2 g) and Et₃N (0.4 ml) in CH2Cl2 (10 ml). The reaction mixture was stirred overnight, then washed with saturated NaHCO₃ solution, the organic layer separated, dried and concentrated. Purification of the residue by column chromatography on alumina, eluting with CHCl₃ afforded the title compound (0.2 g). m.p. 155°–7° C.

¹H-Nmr (CDCl₃) δ: 8.28 (d, 1H), 7.77 (d, 1H), 6.96–6.85 (m, 2H), 6.68 (t, 1H), 4.60–4.47 (m, 1H), 3.08 (m, 2H), 2.98 (q, 2H), 2.42 (s, 3H), 2.57–2.45 (m, 2H), 2.05–1.90 (m, 3H), 1.44 (t, 3H), 1.55–1.30 (m, 3H), 1.10–1.00 (m, 2H).

EXAMPLE 9

(endo)-N-(8-Methyl-8-azabicyclo[3.3.1]non-3-yl)-3,3-3ethylimidazo[1,5-a]plyridin-1-carboxamide (E9)

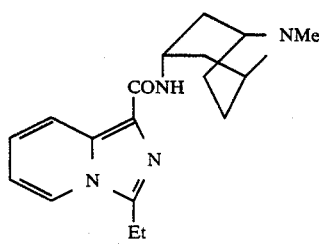

Following the procedure outlined in Example 8,3-ethylimidazo(1,5-a)pyridin-1-carboxylic acid (D4) (0.70 g) was converted to the title compound (0.9 g). m.p. 107°–8° C.

¹H-Nmr (CDCl₃) δ: 8.25 (dm, 1H), 7.77 (dm, 1H), 7.71 (brd, 1H), 6.94 (dd, 1H), 6.69 (tm, 1H), 4.11 (q, 1H), 3.20 (brs, 2H), 2.96 (q, 2H), 2.32 (s, 3H), 2.35–2.10 (m, 3H), 2 05–1.95 (m, 3H), 1.82 (brd, 2H), 1.46 (t, 3H),

EXAMPLE 10

N-(3-Quinuclidinyl)-3-ethylimidazo[1,5-a]pyridin-1-carboxamide hydrochloride (E10)

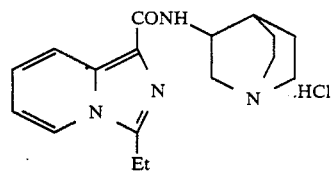

Following the procedures outlined in Example 8,3-ethylimidazo[1,5-a]pyridin-1-carboxylic acid (0.7 g) was converted to the title compound (E10) (0.5 g), isolated as the hydrochloride salt. m.p. 186°–9° C.

¹H-Nmr (d⁶-DMSO) δ: 11.80 (brs, 1H), 8.80 (brs, 1H), 8.30 (d, 1H), 8.12 (d, 1H), 7.20 (t, 1H), 6.99 (t, 1H), 4.60–4.50 (m, 1H), 3.80–3.10 (m, 8H), 50–2 40 (m, 2H), 2.15–1.80 (m, 3H), 1 52 (t, 3H).

EXAMPLE 11

(endo)-N-(8-Methyl-8-azabicyclo[3,2,1]oct-3-yl)-3-trifluoromethvlimidazo[1,5-a]pyridin-1-carboxamide hydrochloride (E11)

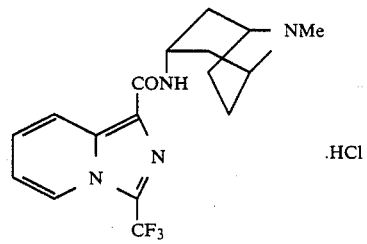

Following the procedures outlined in Example 8,3-trifluoromethylimidazo[1,5-a]pyridin-1-carboxylic acid (D5) (0.6 g) was converted to the title compound (0.75 g) isolated as its hydrochloride salt. m.p. 2.60°–1° C.

¹H-Nmr (CDCl₃) δ: 12.45 (brs, 1), 8.42 (d, 1), 8.20 (d, 1), 7.41 (d, 1), 7.30–7.20 (m, 1), 7.00 (t, 1), 4.41 (q, 1), 3.84 (brs, 2), 3.26–3.15 (m, 2), 2.80 (d, 3), 2.50–2.10 (m, 4), 1.93 (brs, 2).

EXAMPLE 12

(endo)-N-(8-Methyl-8-azabicyclo[3,2,1oct-3-yl)-3-acetylindolizin-1-carboxamide (E12)

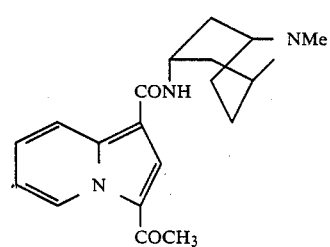

Following the procedure outlined in Example 2;3-acetylindolizin-1-carboxylic acid (D6) (0.4 g) was converted to the title compound (E12) (0.25 g). m.p. 211° C.

¹H-Nmr (CDCl₃) δ: 9.99 (d, 1), 8.47 (dm, 1), 7.55 (s, 1), 7.36 (ddm, 1), 7.01 (t, 1), 6.27 (brd, 1), 4.32 (q, 1), 3.22

(brs, 2) 2.60 (s, 3), 2.32 (s, 3), 2.40–2.20 (m, 3), 1.95–1.75 (m, 5H).

EXAMPLE 13

(endo)-N-(8-Methyl-8-azabicyclo[3.2.1]octan-3-yl)-3,3-dimethylindene-1-carboxamide monohydrochloride (E13)

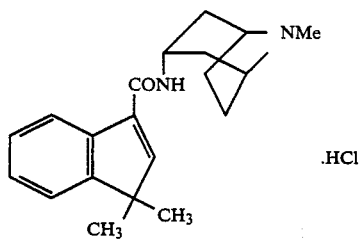
(E13)

A stirred solution of 3,3-dimethylindene-1-carbonyl chloride (T. Kurihara et al. Heterocycles, 1985, 23, (3) 557) (1.1 g) in dry CH$_2$Cl$_2$ (50 ml) at 0° C. was treated with a solution of (Endo)-8-methyl-8-azabicyclo[3.2.1]-octan-3-amine (0.8 g) in dry CH$_2$Cl$_2$ (50 ml). After 2h, the reaction mixture was diluted with ether (300 ml) and the title compound was collected and dried (1.6 g) m.p. >300° C.

$^1$H NMR ($\delta$, d$^6$-DMSO): 11.90–10.30 (br s, 1H), 8.20 (m, 1H), 7.80–7.70 (m, 1H), 7.50–7.45 (m, 1H), 7.30–4.20 (m, 2H), 7.04 (s, 1H), 4.00–3.60 (m, 2H), 2.69 (s, 3H), 2.70–2.10 (m, 8H), 1.31 (s, 6H).

EXAMPLE 14

(endo)-N-(8-Methyl-8-azabicyclo[3.3.1]non-3-yl)-3,3-dimethylindene-1-carboxamide (E14)

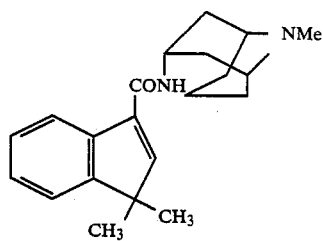
(E14)

The title compound was prepared in a similar manner to that described in Example 13 m.p. 194°–5° C.

EXAMPLE 15

(endo)-N-(1-Azabicyclo[2.2.2.]oct-3-yl)-3,3-dimethylindene-1-carboxamide monohydrochloride (E15)

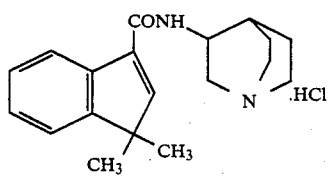
(E15)

The title compound was prepared in a similar manner to that described in Example 13 m.p. 267°–272° C.

EXAMPLE 16

(endo)-8-Methyl-8-azabicyclo[3.2.1]oct-3-yl]-3,3-dimethylindene-1-carboxylate ester hydrochloride (E16)

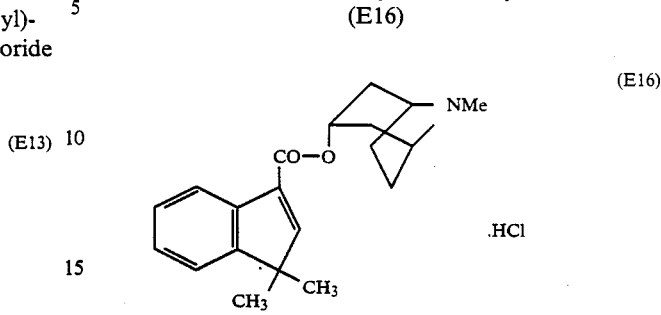
(E16)

A stirred solution of tropine (0.403 g) in dry THF (10 ml) at 0° C. was treated with n-BuLi (1.1eq, 1.838 ml, 1.55M in hexane). After 30 minutes, a solution of 3,3-dimethylindene-1-carbonyl chloride (0.535 g) in THF (10ml) was added, the reaction was allowed to warm to room temperature and stirred overnight.

The reaction was washed with saturated aqueous NaHCO$_3$ and the aqueous layer extracted with Et$_2$O. The organic layer was dried (NaSO), filtered and evaporated to dryness.

The residue was taken up in EtOH (10 ml) and ethanolic HCl (1.79 ml, 1.31M solution) added. The solution was cooled and the title compound collected and dried (0.638 g). m.p. 227°–235° C.

$^1$H-Nmr (d6 DMSO) $\delta$: 10.89 (brs, 1H), 7.87 (m, 1H), 7.50 (m, 1H), 7.38 (s, 1H), 7.30 (s, 1H), 5.15 (m, 1H), 3.87 (brs, 2H), 2.80–2.55 (m, 5H), 2.32–1.90 (m, 6H), 1.35 (s, 6H).

EXAMPLE 17

(endo)-N-(8-Methyl-8-azabicyclo[3.2.1]octan-3-yl)azulene-1-carboxamide (E17)

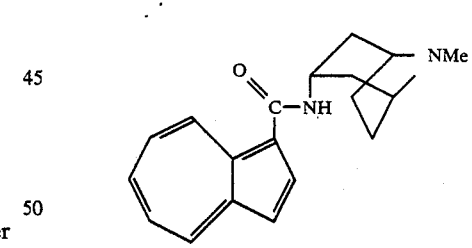
(E17)

A solution of azulene-1-carbonyl chloride (W. Treibs et al., Chem. Ber., 92, 1216 [1959]) (0.56 g) in CH$_2$Cl$_2$ (100 ml) at 0° C. was treated with a solution of (endo)-8-methyl-8-azabicyclo[3.2.1]octan-3-amine (0.42 g) and triethylamine (0.3 g) in CH$_2$Cl$_2$ (10 ml) and the reaction mixture stirred at room temperature for 2h. The organic solution was washed with saturated NaHCO$_3$ solution, dried (K$_2$CO$_3$) and evaporated to dryness under reduced pressure. Recrystallisation from EtOAc/petrol afforded the title compound (0.45 g). m.p. 107°–8° C.

$^1$H nmr (CDCl$_3$) $\delta$: 9.70 (d, 1H),
0 8.43 (d, 1H), 7.94 (d, 1H), 7.77 (t, 1H), 7.49 (t, 1H), 7.37 (t, 1H), 7.29 (d, 1H), 6.57 (brd, 1H), 4.38 (q, 1H), 3.26 (brs, 2H), 2.42–2.15 (m, 7H including 2.35, s, 3H, 2.00–1.80 (m, 4H, m.s. M+ 294.1745; C$_{19}$H$_{22}$N$_2$O requires 294.1758.

EXAMPLE 18

(endo)-N-(8-Methyl-8-azabicyclo[3.2.1]octan-3-yl) 3-methyl azulene-1-carboxamide monohydrochloride (E18)

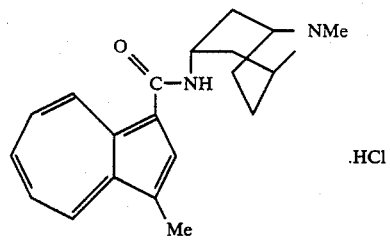

The title compound m.p. 165°–70° C., was prepared using 3-methyl azulene-1-carbonyl chloride in place of azulene-1-carbonyl chloride by an analogous procedure to that described in Example 17

3-Methyl azulene-1-carbonyl chloride was prepared in situ from 3-methyl azulene-1-carboxylic acid (R. N. McDonald et al., J. Org. Chem., 41, 1822 [1976] by addition of one equivalent of oxalyl chloride to a solution of the acid in dichloromethane.

Pharmacology

Antagonism of the von Bezold-Jarisch reflex

The compounds were evaluated for antagonism of the von Bezold-Jarisch reflex evoked by 5-HT in the anesthetized rat according to the following method Male rats 250–350 g, were anesthetized with urethane (1.25 g/kg intraperitoneally) and blood pressure and heart rate recorded as described by Fozard J. R. et al., J. Cardiovasc Pharmacol 2, 229–245 (1980). A submaximal dose of 5-HT (usually 6 μg/kg) was given repeatedly by the intravenous route and changes in heart rate quantified Compounds were given intravenously and the concentration required to reduce the 5-HT-evoked response to 50% of the control response ($ED_{50}$) was then determined. The results are as shown in Table 1.

TABLE 1

| Compound | $ED_{50}$ μg/kg i.v. |
|---|---|
| 2 | 0.24 |
| 8 | 0.5 |
| 9 | 1.0 |
| 13 | 1.1 |
| 17 | 13 |

I claim:

1. A compound of formula (I), or a pharmaceutically acceptable salt thereof:

Y-CO-L-Z      (I)

wherein

L is NH or O;

Y is a group of formula (a);

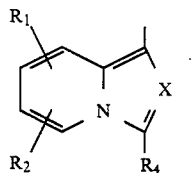

wherein $R_1$ and $R_2$, are independently selected from hydrogen or halogen;

X is N or $CR_3$ wherein $R_3$ is hydrogen or $C_{1-6}$ alkoxy;

$R_4$ is hydrogen, halogen, $CF_3$, $C_{1-6}$ alkyl, $C_{1-6}$ alkoxy, $C_{1-6}$ alkylthio, $C_{1-6}$ alkylsulphonyl, $C_{1-6}$ alkylsulphinyl, $C_{1-7}$ acyl, cyano, $C_{1-6}$ alkoxycarbonyl, $C_{1-7}$ acylamino, hydroxy, nitro or amino, aminocarbonyl, or aminosulphonyl, optionally N-substituted by one or two groups selected from $C_{1-6}$ alkyl, $C_{3-8}$ cycloalkyl, and $C_{3-8}$ cycloalkyl $C_{1-4}$ alkyl or disubstituted by $C_4$ or $C_5$ polymethylene; phenyl or phenyl $C_{1-4}$ alkyl group optionally substituted in the phenyl ring by one or two of halogen, $C_{1-6}$ alkoxy or $C_{1-6}$ alkyl groups;

Z is a group of formula (d), (e) or (f):

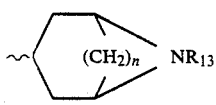

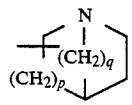

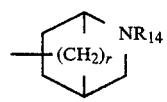

wherein n is 2 or 3;

p is 1 or 2;

q is 1 to 3;

r is 1 to 3; and $R_{13}$ or $R_{14}$ is $C_{1-4}$ alkyl.

2. A compound according to claim 1, of formula (II):

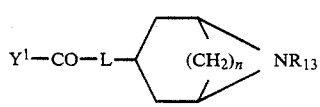

wherein $Y^1$ is a group of formula (a) wherein X is N, CH or C—OCH$_3$, as defined in claim 1, and the remaining variables are as defined in claim 1.

3. A compound according to claim 1, of formula (III):

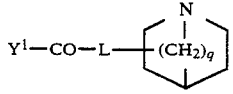

wherein $Y^1$ is a group of formula (a) wherein X is N, CH or C—OCH$_3$, as defined in claim 1, $q^1$ is 1 or 2 and the remaining variables are as defined in claim 1.

4. A compound according to claim 1 of formula (IV):

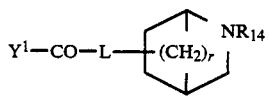

wherein $Y^1$ is a group of formula (a) wherein X is N, CH or C—OCH$_3$, as defined in claim 1, $R^1$ is 1 or 2 and the remaining variables are as defined in claim 1.

5. A compound according to claim 1, wherein Y is of formula (a) as defined in claim 1, wherein $R_4$ is an ethyl group.

6. A compound according to claim 1 wherein $R_1$ and $R_2$ are both hydrogen.

7. A compound selected from the group consisting of:
(endo)-N-(8-methyl-8-azabicyclo[3.2.1]oct-3-yl)indolizin-1-carboxamide,
(endo)-N-(8-methyl-8-azabicyclo[3.2.1]oct-3-yl)-3-ethylindolizin-1-carboxamide, N-(3-quinuclidinyl)-3-ethylindolizin-1-carboxamide,
N-(2-methyl-2-azabicyclo[2,2,2]oct-5-yl)-3-ethylindolizin-1-carboxamide,
(endo)-N-(8-methyl-8-azabicyclo[3.2.1]oct-3-yl)-3-methylindolizin-1-carboxamide,
(endo)-N-(8-methyl-8-azabicyclo[3, 2,1]oct-3-yl)-3-bromoindolizin-1-carboxamide,
(endo)-N-(9-methyl-9-azabicyclo[3.3.1]non-3-yl)-3-ethylimidazo[1,5-a]pyridin-1-carboxamide,
(endo)-N-(8-methyl-8-azabicyclo[3, 2,1]oct-3-yl)-3-ethylimidazo[1,5-a]pyridin-1-carboxamide,
N-(3-quinuclidinyl)-3-ethylimidazo[1,5-a]-pyridin-1-carboxamide,
(endo)-N-(8-methyl-8-azabicyclo[3, 2,1]oct-3-yl)-3trifluoromethylimidazo[1,5-a]pyridin-1-carboxamide,
(endo)-N-(8-methyl-8-azabicyclo[3,2,1]oct-3-yl)-2-triacetylindolizin-1-carboxamide,
and hydrochloride salts of any of the foregoing.

8. A pharmaceutical composition for use in the treatment of migraine, cluster headache, trigeminal neuralgia or emesis, comprising a non-toxic effective amount of a compound according to claim 1, and a pharmaceutically acceptable carrier.

9. A method of treatment of migraine, cluster headache, trigeminal neuralgia or emesis in mammals, which comprises the administration of a non-toxic effective amount of a compound according to claim 1.

* * * * *